(12) United States Patent
Lehtonen

(10) Patent No.: US 9,956,056 B2
(45) Date of Patent: May 1, 2018

(54) MEDICAL OR A DENTAL INSTRUMENT AND A METHOD FOR MANUFACTURING THE SAME

(71) Applicant: LM-INSTRUMENTS OY, Parainen (FI)

(72) Inventor: Kari Lehtonen, Parainen (FI)

(73) Assignee: LM-INSTRUMENTS OY, Parainen (FI)

( * ) Notice: Subject to any disclaimer, the term of this patent is extended or adjusted under 35 U.S.C. 154(b) by 0 days. days.

(21) Appl. No.: 14/891,830

(22) PCT Filed: May 14, 2014

(86) PCT No.: PCT/FI2014/050363
§ 371 (c)(1),
(2) Date: Nov. 17, 2015

(87) PCT Pub. No.: WO2014/184441
PCT Pub. Date: Nov. 20, 2014

(65) Prior Publication Data
US 2016/0128799 A1    May 12, 2016

(30) Foreign Application Priority Data

May 17, 2013   (FI) ..................... 20135531

(51) Int. Cl.
*A61C 3/00*      (2006.01)
*A61B 90/98*     (2016.01)
(Continued)

(52) U.S. Cl.
CPC ............... *A61C 3/00* (2013.01); *A61B 90/90* (2016.02); *A61B 90/98* (2016.02); *A61B 2017/00526* (2013.01); *A61C 2204/005* (2013.01)

(58) Field of Classification Search
CPC ..... A61C 3/00; A61C 2204/005; A61B 90/98; A61B 2017/00526; A61B 90/90
(Continued)

(56) References Cited

U.S. PATENT DOCUMENTS 5,501,597 A    3/1996  Wilson
6,322,362 B1   11/2001  Holms
(Continued)

FOREIGN PATENT DOCUMENTS

WO    2008062387 A2    5/2008

*Primary Examiner* — Nicholas Lucchesi
(74) *Attorney, Agent, or Firm* — Fay Sharpe LLP

(57) ABSTRACT

A medical or a dental instrument comprises an operative portion (101) for operations according to the purpose of use of the instrument, a center portion (103) mechanically connecting to the operative portion, and a radio frequency identifier (106) located on the center portion and capable of being read from a distance of the instrument. The instrument further comprises a tubular handle portion (104) provided to surround the radio frequency identifier and at least a part of the center portion, the tubular handle portion being cast on the instrument so that the material of the tubular handle portion is adhered to the material of the center portion. Thus, the tubular handle portion acts not only as the handle portion but also as at least a part of a fixation system attaching the radio frequency identifier to the instrument. An instrument of such construction is easy to keep hygienic.

14 Claims, 3 Drawing Sheets

(51) Int. Cl.
*A61B 90/90* (2016.01)
*A61B 17/00* (2006.01)

(58) Field of Classification Search
USPC .......................................... 433/29, 141–148
See application file for complete search history.

(56) References Cited

U.S. PATENT DOCUMENTS

| | | | |
|---|---|---|---|
| 2006/0043178 A1* | 3/2006 | Tethrake | G06K 19/07749 235/385 |
| 2006/0119481 A1* | 6/2006 | Tethrake | A61B 50/10 340/572.1 |
| 2006/0244652 A1* | 11/2006 | Tethrake | A61B 90/00 342/44 |
| 2007/0159336 A1 | 7/2007 | Tethrake | |
| 2008/0200926 A1* | 8/2008 | Verard | A61B 5/06 606/130 |
| 2009/0184825 A1* | 7/2009 | Anderson | G06Q 10/087 340/572.1 |
| 2010/0281636 A1* | 11/2010 | Ortins | A46B 9/04 15/4 |
| 2012/0107770 A1 | 5/2012 | Beach | |
| 2014/0120492 A1* | 5/2014 | Ioannidis | A61C 19/043 433/27 |
| 2014/0125482 A1* | 5/2014 | Rigsby | A61B 19/44 340/539.13 |
| 2016/0110637 A1* | 4/2016 | Lehovetzki | B25B 15/02 235/492 |
| 2016/0140432 A1* | 5/2016 | Lehovetzki | B25B 13/04 235/492 |

* cited by examiner

MEDICAL OR A DENTAL INSTRUMENT AND A METHOD FOR MANUFACTURING THE SAME

FIELD OF THE INVENTION

The invention relates to a medical or a dental instrument and to a method for manufacturing the same.

BACKGROUND

In many cases, authorities and actors of the medical or dental field want to have an infallible and traceable solution to follow instruments so as be able to trace disinfection, sterilization, reparation, and other operations directed to or carried out with the instruments under consideration. Nowadays, users do not typically have the time and willingness to generate reports manually because of the related workload. In addition, there is a risk of errors with manual data recording and identification of instruments, which prevents regarding the manually recorded data as an irrefutable proof of what has been done and what has been not done.

A known solution uses tags including a radio frequency identifier "RFID". The tag is glued on the instrument to be identified. It is however challenging to provide a glue joint that produces a reliable long term adhesion of the tag on the instrument in cases where the instrument is exposed to operations such as sterilization, disinfection, and/or ultrasonic baths.

WO2008062387 describes an instrument comprising a radio frequency identifier. The radio frequency identifier is embedded in a polymer sheet that is attached on a surface of the handle of the instrument. The polymer sheet that includes the radio frequency identifier can be, for example, wrapped around the handle of the instrument. In order to obtain an even surface, it is possible to provide the instrument with a recess corresponding in size to the polymer sheet. In an advantageous embodiment described in WO2008062387, the polymer sheet comprises two layers between which the radio frequency identifier is located. The two layers are made of materials having different hardness. The layer of the harder material is against the instrument in order to obtain a better adhesion. The softer material protects the radio frequency identifier against external impacts. It may be, however, in some circumstances hard to guarantee that the polymer sheet remains firmly attached to the instrument. Furthermore, it may be hard to guarantee that no slits are left between the polymer sheet and the handle of the instrument. The slits are undesirable because, in some circumstances, they may collect impurities.

SUMMARY

The following presents a simplified summary in order to provide a basic understanding of some aspects of various embodiments of the invention. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the invention, there is provided a new method for manufacturing a medical or a dental instrument that comprises an operative portion for operations according to the purpose of use of the instrument, a center portion mechanically connecting to the operative portion, and a radio frequency identifier. A method according to the invention comprises:
  placing the radio frequency identifier on the center portion of the instrument, and
  providing a tubular handle portion to surround the radio frequency identifier and at least a part of the center portion by casting the tubular handle portion on the instrument so that the material of the tubular handle portion gets adhered to the material of the center portion and so that the radio frequency identifier is located between the tubular handle portion and the center portion after the casting.

The benefit of casting the tubular handle portion on the instrument so that the material of the tubular handle portion is adhered to the material of the center portion is that there are no such slits between the tubular handle portion and the center portion which would collect impurities, and thus it is easier to keep the instrument hygienic. Therefore, the method according to the invention provides an instrument where the tubular handle portion acts not only as the handle portion for providing a gripping surface of the instrument but also as at least a part of a fixation system that:
  attaches the radio frequency identifier to the instrument, and furthermore
  is easy to keep hygienic.

The tubular handle portion is advantageously made of material whose electrical resistivity is sufficiently high so that the operation of the radio frequency identifier is not hindered. The electrical resistivity is advantageously at least $10^{-3}$ $\Omega$m at 20° C. More advantageously, the tubular handle portion is made of electrically non-conductive material.

In an instrument according to an advantageous and exemplifying embodiment of the invention, the material of the tubular handle portion is mechanically softer than the material of the center portion. Thus, the center portion can be arranged to provide the required mechanical stiffness and the tubular handle portion can be arranged to enable a user to have a good grip on the instrument with a relatively small pressing force.

In accordance with the invention, there is provided also a new medical or dental instrument that comprises:
  an operative portion for operations according to the purpose of use of the instrument,
  a center portion mechanically connecting to the operative portion,
  a radio frequency identifier on the center portion and capable of being read from a distance of the instrument and capable of storing information, and
  a tubular handle portion provided to surround the radio frequency identifier and at least a part of the center portion so that the radio frequency identifier is located between the tubular handle portion and the center portion, the tubular handle portion being cast on the instrument so that the material of the tubular handle portion is adhered to the material of the center portion.

A number of non-limiting and exemplifying embodiments of the invention are described in accompanied dependent claims.

Various non-limiting and exemplifying embodiments of the invention both as to constructions and to methods of manufacturing, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of unrecited features. The features recited in depending claims are mutually freely combinable unless otherwise explicitly stated. Furthermore, it is to be understood that the use of "a" or "an", i.e. a singular form, throughout this document does not exclude a plurality.

BRIEF DESCRIPTION OF THE FIGURES

Exemplifying embodiments of the invention and their advantages are explained in greater detail below in the sense of examples and with reference to the accompanying drawings, in which.

DESCRIPTION OF EXEMPLIFYING EMBODIMENTS

Figure 1A:
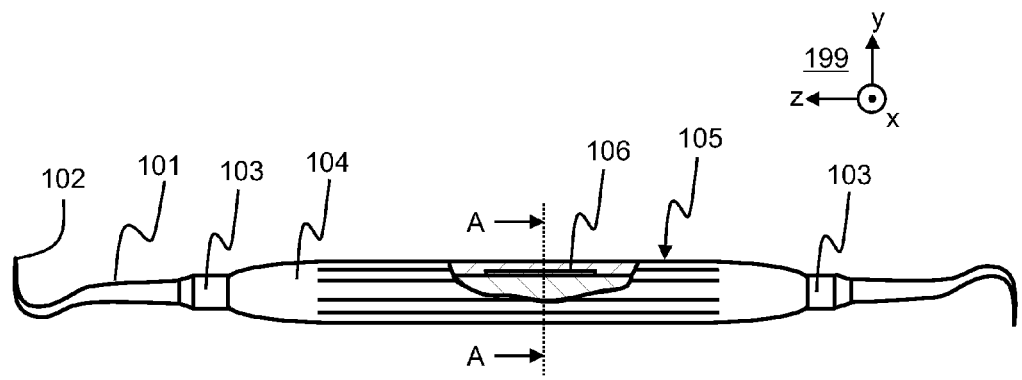
FIGS. 1a and 1b illustrate an instrument according to an exemplifying embodiment of the invention.
Figure 1B:
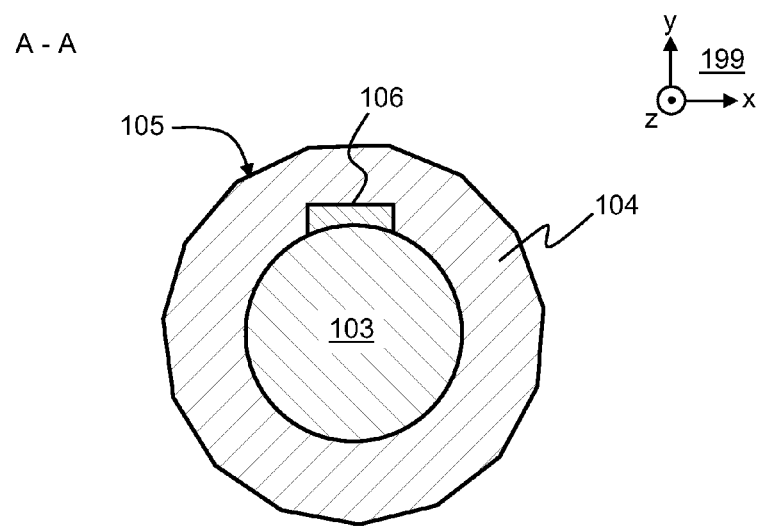

FIG. 1a shows a partial section view of an instrument according to an exemplifying embodiment of the invention. FIG. 1b shows a view of a section taken along the line A-A shown in FIG. 1a. The section plane is parallel with the xy-plane of a coordinate system 199. The instrument illustrated in FIGS. 1a and 1b is obtainable with a method according to an exemplifying embodiment of the invention. In the exemplifying case illustrated in FIGS. 1a and 1b, the instrument is a dental instrument suitable for e.g. removing dental calculus. The instrument comprises an operative portion 101 that has a tip portion 102 for performing the operations according to the purpose of use of the instrument. The instrument comprises a center portion 103 that constitutes a mechanical support core of the instrument and is mechanically connected to the operative portion 101 as illustrated in FIG. 1a. In the exemplifying case illustrated in FIGS. 1a and 1b, the instrument comprises operative portions 102 at its both ends. It is, however, also possible that an instrument according to an exemplifying embodiment of the invention comprises an operative portion 102 at only one end. The instrument comprises a radio frequency identifier "RFID" 106 capable of being read from a distance of the instrument and capable of storing information. The information may contain for example identifying information identifying the instrument as an individual object from among similar instruments and/or information indicating e.g. a date of manufacture of the instrument, the manufacturer of the instrument and/or some other information related directly or indirectly to the instrument. The instrument further comprises a tubular handle portion 104 that has been mold cast to surround the radio frequency identifier 106 and at least a part of the center portion 103 so that the material of the tubular handle portion 104 is adhered to the material of the center portion. The above-mentioned radio frequency identifier 106 is located between the center portion 103 and the tubular handle portion 104 as illustrated in FIGS. 1a and 1b. The benefit of the structure where the material of the tubular handle portion 104 is adhered to the material of the center portion 103 is that there are no such slits between the tubular handle portion 104 and the center portion 103 which could collect impurities, and thus the instrument is easier to keep hygienic. Thus, the tubular handle portion 103 acts not only as the handle portion for providing a gripping surface 105 of the instrument but also as at least a part of a fixation system attaching the radio frequency identifier 106 to the instrument. An instrument of such construction is easy to keep hygienic.

The tubular handle portion 104 is advantageously made of material whose electrical resistivity is sufficiently high so that the operation of the radio frequency identifier 106 is not hindered. The electrical resistivity is advantageously at least $10^{-3}$ Ωm at 20° C. More advantageously, the tubular handle portion 104 is made of electrically non-conductive material.

In an instrument according to an exemplifying embodiment of the invention, the material of the tubular handle portion 104 is mechanically softer than the material of the center portion 103. The center portion 103 can be arranged to provide the required mechanical stiffness whereas the tubular handle portion 104 can be arranged to enable a user to have a good grip on the instrument with a relatively small pressing force.

In an instrument according to an exemplifying embodiment of the invention, the material of the center portion 103 is one whose modulus of elasticity is at least 1000 MPa. Examples of materials fulfilling this criterion include metals such as aluminum, titanium and magnesium, stainless steels and also some stiff polymers. The center portion 130 must be stiff enough so that upon use of the instrument, when forces act on the instrument tending to bend it, the radio frequency identifier 106 does not get loose or even break.

In an instrument according to an exemplifying embodiment of the invention, the material of the tubular handle portion 104 is preferably silicone or other suitable elastomer, not only because of its properties in view of gripping the instrument but also since these materials are flexible and soft enough to protect the radio frequency identifier 106 against impacts.

As an alternative to the structure of the instrument shown in FIG. 1a, the tubular handle portion 104 may be arranged to extend over the entire center portion 103 and to cover even part of the operative portion 101.

Figure 2A:
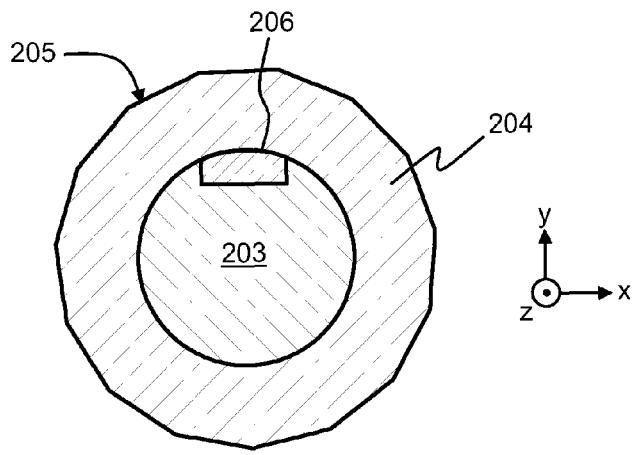
FIGS. 2a, 2b and 2c show cross-sections of instruments according to exemplifying embodiments of the invention.

FIG. 2a shows a cross-section of an instrument according to an exemplifying embodiment of the invention. The cross-section shown in FIG. 2a corresponds to the cross-section shown in FIG. 1b. The instrument comprises an operative portion for performing the operations according to the purpose of use of the instrument, which operative portion is not shown in FIG. 2a, however. The instrument comprises a center portion 203 that constitutes a mechanical support core of the instrument and is mechanically connected to the operative portion. The instrument comprises a tubular handle portion 204 surrounding at least a part of the center portion 203 and constituting a gripping surface 205 of the instrument. The instrument further comprises a radio frequency identifier "RFID" 206 capable of being read from a distance of the instrument and capable of storing information. The radio frequency identifier 206 is located between the center portion 203 and the tubular handle portion 204 as illustrated in FIG. 2a. In this exemplifying case illustrated in FIG. 2a, the center portion 203 comprises a cavity for the radio frequency identifier 206.

Figure 2B:
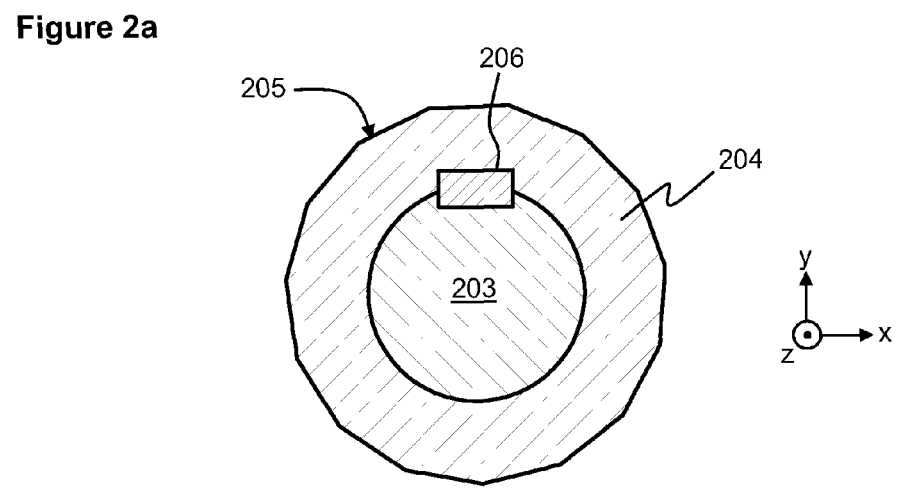

FIG. 2b shows a cross-section of an instrument according to an exemplifying embodiment of the invention. The cross-section shown in FIG. 2b corresponds to the cross-section shown in FIG. 1b. In the exemplifying case illustrated in FIG. 2b, both the center portion 203 and the tubular handle portion 204 comprise a cavity for the radio frequency identifier 206.

Figure 2C:
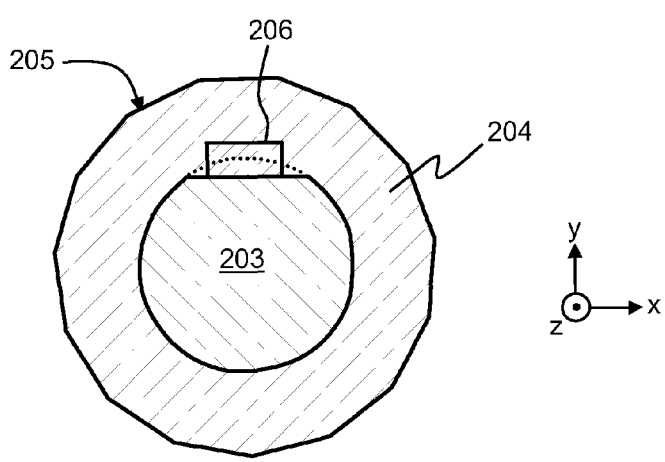

FIG. 2c shows a cross-section of an instrument according to an exemplifying embodiment of the invention. The cross-section shown in FIG. 2c corresponds to the cross-section shown in FIG. 1b. In the exemplifying case illustrated in FIG. 2c, the center portion 203 comprises a flat facet for the radio frequency identifier 206. In one preferable embodiment, the facet could rather be described being a small cavity arranged on the surface of a basically cylindrical center portion 203. In one preferable embodiment, dimensions of the cavity correspond to those of the radio frequency identifier 206.

Figure 3:
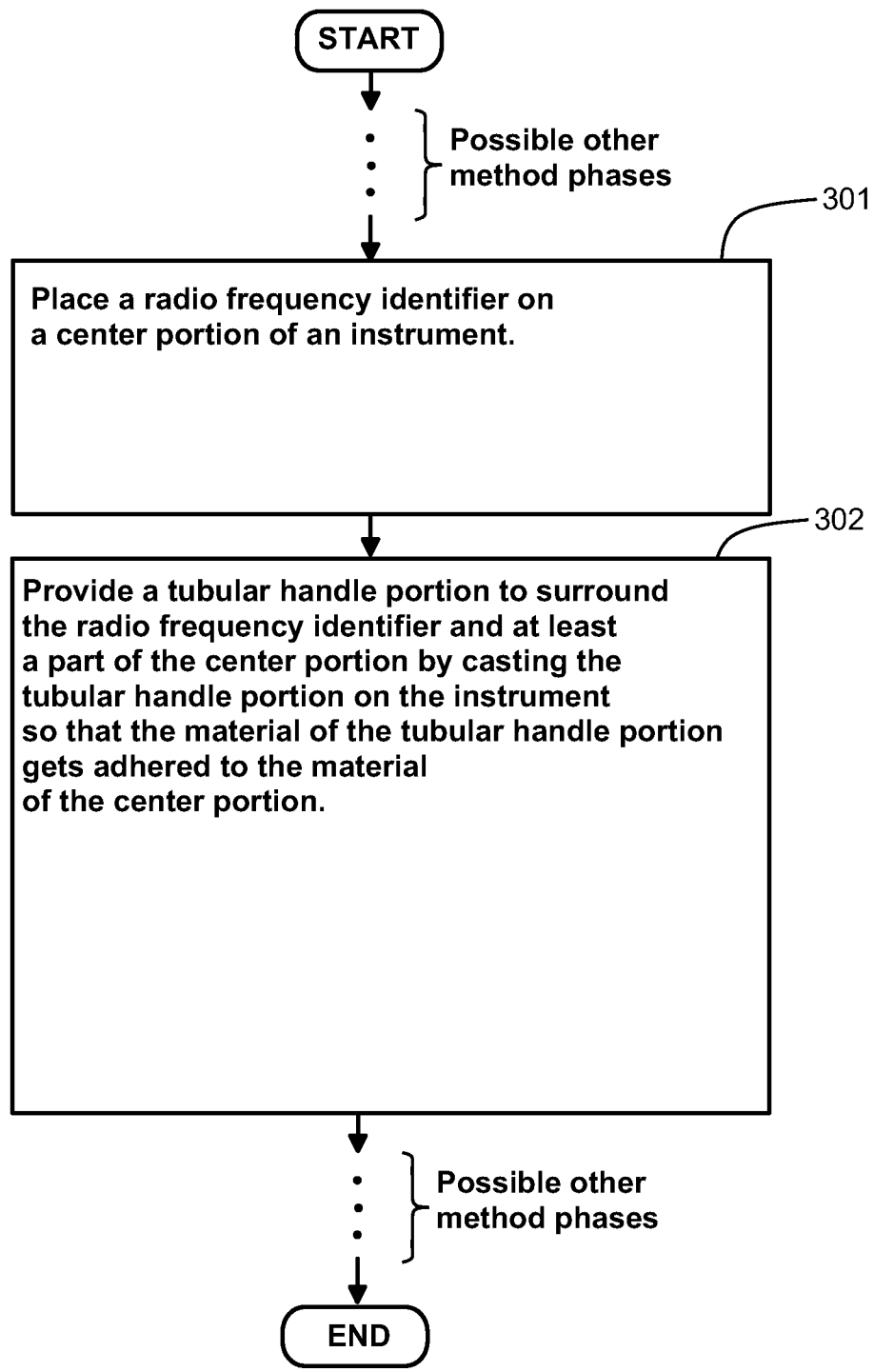
FIG. 3 shows a flowchart of a method according to an exemplifying embodiment of the invention for manufacturing a medical or a dental instrument.

FIG. 3 shows a flowchart of a method according to an exemplifying embodiment of the invention for manufacturing an instrument that comprises an operative portion for operations according to the purpose of use of the instrument, a center portion mechanically connecting to the operative portion, and a radio frequency identifier. The method comprises the following actions:

action 301: placing the radio frequency identifier on the center portion of the instrument, and subsequently action 302: providing a tubular handle portion to surround the radio frequency identifier and at least a part of the center portion by casting the tubular handle portion on the instrument so that the material of the tubular handle portion gets adhered to the material of the center portion.

In a method according to an exemplifying embodiment of the invention, placing of the radio frequency identifier on the center portion of the instrument comprises attaching the radio frequency identifier to the surface of the center portion with adhesive material.

In a method according to another exemplifying embodiment of the invention, the center portion of the instrument is arranged to comprise a cavity with dimension corresponding to those of the radio frequency identifier to ensure that the radio frequency identifier remains at its desired position during casting of the tubular hand portion on the instrument.

According to the current understanding of the applicant, the various aspects and benefits of the invention are best achievable by a construction in which a tubular handle portion surrounds the radio frequency identifier and at least a part of the center portion of the instrument, in which the tubular handle portion is cast on the instrument so that material of the tubular handle portion is adhered to material of the center portion, in which the material of the tubular handle portion is silicone or some other elastomer which is mechanically softer than the material of the center portion, while the center portion whose modulus of elasticity is at least 1000 MPa constitutes a mechanical support core of the instrument, and wherein the center portion comprises a cavity for the radio frequency identifier.

The specific examples provided in the description given above should not be construed as limiting the applicability and/or the interpretation of the appended claims.

What is claimed is:

1. A dental instrument comprising:
an elongated handle portion comprised of silicone or other elastomer,
a body portion having operative portions at ends of the body portion, the body portion mechanically connecting to the operative portions, said body portion and operative portions being comprised of titanium, magnesium, stainless steel or aluminum, and
a radio frequency identifier capable of being read from a distance of the instrument and capable of storing information, said radio frequency identifier disposed partially within a cavity in the body portion,
wherein the radio frequency identifier is covered by the elongated handle portion and partially disposed in a cavity in the elongated handle portion so that the radio frequency identifier is located between the handle portion and the body portion, the elongated handle portion being cast over the radio frequency identifier so that a material of the elongated handle portion is adhered to a material of the body portion and to the radio frequency identifier such that the radio frequency identifier is fixed on the body portion by the elongated handle portion.

2. An instrument according to claim 1, wherein electrical resistivity of the material of the elongated handle portion is at least $10^{-3}$ Ωm at 20° C.

3. An instrument according to claim 1, wherein the material of the elongated handle portion is electrically non-conductive.

4. An instrument according to claim 1, wherein the material of the elongated handle portion is mechanically softer than the material of the body portion and the body portion constitutes a mechanical support core of the dental instrument.

5. An instrument according to claim 1, wherein modulus of elasticity of the material of the body portion is at least 1000 MPa.

6. The dental instrument of claim 1, wherein there are no slits between the elongated handle portion and the body portion which could collect impurities.

7. The dental instrument of claim 1, wherein said elongated handle portion is comprised of silicone.

8. The dental instrument of claim 1, wherein said body portion and operative portions are comprised of aluminum.

9. The method of claim 1, wherein said body portion is comprised of titanium, magnesium, stainless steel, or aluminum.

10. The method of claim 9, wherein said body portion is comprised of aluminum.

11. The method of claim 10, wherein said tubular handle portion is comprised of silicone.

12. A method for manufacturing a dental instrument comprising an elongated handle portion having operative portions at the ends of the elongated handle portion for operations according to a purpose of use of the dental instrument, a body portion between the operative portions mechanically connecting to the operative portions, and a radio frequency identifier, the method comprising:
placing the radio frequency identifier partially within a cavity on the body portion of the dental instrument, and wherein the method further comprises:
providing a tubular handle portion to surround the radio frequency identifier and at least a part of the body portion by casting the tubular handle portion on the radio frequency identifier and body portion so that a material of the tubular handle portion is adhered to a material of the body portion and so that the radio frequency identifier is partially housed within a cavity in the tubular handle portion and is fixed between the tubular handle portion and the body portion after the casting.

13. A method according to claim 12, wherein placing of the radio frequency identifier on the body portion of the instrument comprises attaching the radio frequency identifier to a surface of the body portion with adhesive material.

14. A method according to claim 12, wherein the body portion cavity includes dimensions corresponding to those of the radio frequency identifier and the radio frequency identifier is placed into said cavity prior to casting the elongated handle portion on the dental instrument.

* * * * *